United States Patent [19]

Wasley

[11] Patent Number: 4,803,197

[45] Date of Patent: Feb. 7, 1989

[54] 2,1-BENZOTHIAZEPINE-2,2-DIOXIDE-5-CARBOXYLIC ACID DERIVATIVES

[75] Inventor: Jan W. F. Wasley, Chatham, N.J.

[73] Assignee: Ciba-Geigy Corporation, Ardsley, N.Y.

[21] Appl. No.: 2,074

[22] Filed: Jan. 12, 1987

[51] Int. Cl.$^4$ .................. C07D 281/02; A61K 31/55
[52] U.S. Cl. ...................................... 514/211; 540/552
[58] Field of Search ........................ 514/211; 540/552

[56] References Cited

U.S. PATENT DOCUMENTS

| | | | |
|---|---|---|---|
| 3,962,261 | 6/1976 | Zinnes et al. | 549/9 |
| 4,185,109 | 1/1980 | Rosen | 546/187 |
| 4,233,299 | 11/1980 | Trummlitz et al. | 424/246 |
| 4,582,850 | 4/1986 | Liauw | 514/431 |
| 4,605,665 | 8/1986 | Liauw | 514/431 |

OTHER PUBLICATIONS

Shen et al., "Non-Steroidal Inhibitors of Arachidonic Acid Metabolism" Butterfield Publishers, Kent, England (1980), pp. 315-317 and 331-335.
J. C. S. Chem. Communications 1981 (20), 1087-8, R. A. Abramovitch et al.
R. A. Abramovitch et al., J. Org. Chem. 49, 3114-21 (1984).
J. Med. Chemistry, 14, 973 (1971).

Primary Examiner—John M. Ford
Attorney, Agent, or Firm—Norbert Gruenfeld

[57] ABSTRACT

Disclosed are the compound of the formula

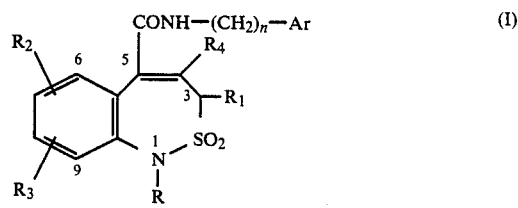

wherein n represents zero, 1 or 2; Ar represents a carbocyclic or heterocyclic aryl radical; R and $R_1$ independently represent hydrogen, lower alkyl or Ar-lower alkyl; $R_2$ and $R_3$ independently represent hydrogen, lower alkyl, halogen, trifluoromethyl or lower alkoxy; or $R_2$ and $R_3$ together on adjacent carbon atoms represent lower alkylenedioxy; $R_4$ represents hydroxy or $NR_5R_6$ wherein $R_5$ and $R_6$ independently represent hydrogen, lower alkyl or AR-lower alkyl,; or $R_5$ and $R_6$ together with the nitrogen to which they are attached represent pyrrolidino or piperidino; pharmaceutically acceptable salts thereof; lower alkyl enol ethers and lower alkanoyl enol esters of compounds of formual I wherein $R_4$ represents hydroxy; as e.g. antiinflammatory agents; methods for preparing said compounds and pharmaceutical compositions comprising said compounds.

13 Claims, No Drawings

2,1-BENZOTHIAZEPINE-2,2-DIOXIDE-5-CARBOXYLIC ACID DERIVATIVES

SUMMARY OF THE INVENTION

The present invention is concerned with certain 1,3-dihydro-2,1-benzothiazepine-2,2-dioxides which are useful in mammals as inhibitors of the chemotactic activation of neutrophils, inhibitors of the lipoxygenase enzyme system and inhibitors of cartilage matrix degradation.

The foregoing attributes render the compounds of the invention primarily useful as a novel class of therapeutic agents for the treatment in mammals of inflammatory conditions such as rheumatoid arthritis. Compounds of the invention are furthermore contemplated to be useful for the treatment of asthma, allergies, osteoarthritis and cardiac ischemia in mammals.

DETAILED DESCRIPTION OF THE INVENTION

The invention more particularly relates to the compounds described below, processes for preparing same, pharmaceutical compositions comprising said compounds, methods of treating e.g. inflammatory conditions, by administration of said compounds and pharmaceutical compositions to mammals in need thereof.

Particularly, the invention relates to the compounds of formula I

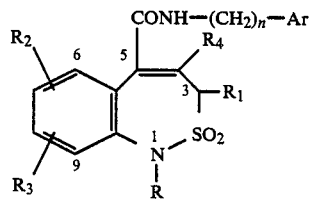

wherein n represents zero, 1 or 2; Ar represents a carbocyclic or heterocyclic aryl radical; R and $R_1$ independently represent hydrogen, lower alkyl or Ar-lower alkyl; $R_2$ and $R_3$ independently represent hydrogen, lower alkyl, halogen, trifluoromethyl or lower alkoxy; or $R_2$ and $R_3$ together on adjacent carbon atoms represent lower alkylenedioxy; $R_4$ represents hydroxy or $NR_5R_6$ wherein $R_5$ and $R_6$ independently represent hydrogen, lower alkyl or Ar-lower alkyl; or $R_5$ and $R_6$ together with the nitrogen to which they are attached represent pyrrolidino or piperidino; pharmaceutically acceptable salts thereof; and lower alkyl enol ethers and lower alkanoyl enol esters of compounds of formula I wherein $R_4$ represents hydroxy.

Certain compounds of formula I can also exist as tautomers which are within the purview of the invention.

Tautomers of the compounds of formula I wherein $R_4$ represents hydroxy or $NHR_5$ correspond to the 4-oxo or imino tautomers, i.e. the 5-carbamoyl-substituted 1,3,4,5-tetrahydro-4-oxo-2,1-benzothiazepine-2,2-dioxides, represented by formula Ia

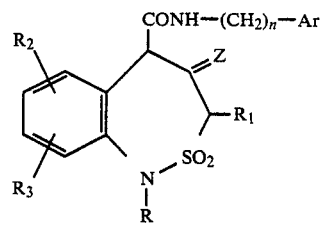

wherein n, Ar, R, $R_1$, $R_2$ and $R_3$ have meaning as defined hereinabove; and Z represents oxygen (O) or $NR_5$ in which $R_5$ represents hydrogen, lower alkyl or Ar-lower alkyl.

More particularly, the invention relates to compounds of formula I wherein Ar represents phenyl or phenyl mono-or di-substituted by one or two radicals selected from lower alkyl, lower alkoxy, lower alkylmercapto, lower alkylsulfinyl, lower alkylsulfonyl, halogen, cyano, carboxy, lower alkoxycarbonyl, carbamoyl and trifluoromethyl; or Ar represents 1- or 2-naphthyl; or Ar represents a five-membered unsaturated heterocyclic radical bonded on carbon and containing one hetero atom selected from sulfur, oxygen, and unsubstituted or lower alkyl substituted amino nitrogen, or a said radicalcontaining two hetero atoms consisting of one imino nitrogen and one member selected from unsubstituted or lower alkyl substituted amino nitrogen, sulfur and oxygen; or Ar represents a six membered unsaturated heterocyclic radical bonded on carbon and containing one or two nitrogen atoms; or Ar represents a bicyclic benzo-fused five membered unsaturated heterocyclic radical bonded on carbon and containing one hetero atom selected from sulfur, oxygen and unsubstituted or lower alkyl substituted amino nitrogen; or Ar represents a bicyclic benzo-fused five membered unsaturated heterocyclic radical bonded on carbon and containing two hetero atoms consisting of one imino nitrogen and one member selected from unsubstituted or lower alkyl substituted amino nitrogen, oxygen and sulfur; or Ar represents a bicyclic benzo-fused 6-membered unsaturated heterocyclic radical bonded on carbon and containing one or two nitrogen atoms; or Ar represents any of said heterocyclic radicals mono- or di-substituted on carbon by lower alkoxy, lower alkyl or halogen; n, R, and $R_1$–$R_6$ are as defined above; pharmaceutically acceptable salts thereof; the corresponding tautomers of formula Ia for said compounds of formula I wherein $R_4$ represents hydroxy or $NHR_5$; lower alkyl enol ethers thereof and lower alkanoyl enol esters thereof when $R_4$ represents hydroxy.

Preferred are the compounds of the invention wherein n represents zero.

Preferred in turn are the compounds of formula I or tautomers thereof wherein Ar represents phenyl or phenyl mono- or di-substituted by one or two radicals selected from lower alkyl, lower alkoxy, lower alkylmercapto, lower alkylsulfinyl, lower alkylsulfonyl, halogen, cyano, carboxy, lower alkoxycarbonyl, carbamoyl and trifluoromethyl; or Ar represents 1- or 2-naphthyl; or Ar represents a heterocyclic aryl radical bonded on carbon to the amide nitrogen and selected from furyl, pyrrolyl, thienyl, thiazolyl, oxazolyl, pyridyl, pyrimidyl, pyrazinyl, benzofuranyl, indolyl, isoquinolyl, quinolyl, imidazolyl, isoxazolyl, benzimidazolyl, benzoxazolyl or any said heterocyclic radical mono- or disubstituted on carbon by lower alkyl, lower alkoxy or halogen, or any of said unsubstituted or substituted pyrrolyl, indolyl, imidazolyl or benzimidazolyl radical substituted on nitrogen by lower alkyl; n represents zero; $R_4$ represents hydroxy; R, $R_1$, $R_2$ and $R_3$ are as defined above; pharmaceutically acceptable salts thereof; lower alkyl enol ethers thereof; and lower alkanoyl enol esters thereof.

Particularly preferred are the compounds of formula I or tautomers thereof wherein n represents zero; Ar represents phenyl or phenyl mono- or disubstituted by one or two radicals selected from lower alkyl, lower alkoxy, lower alkylmercapto, lower alkylsulfinyl, lower alkylsulfonyl, halogen and trifluoromethyl; or Ar represents a heterocyclic radical which is bonded on carbon to the amide nitrogen and is selected from furyl, pyrrolyl, thienyl, thiazolyl, oxazolyl, pyridyl, pyrimidyl, pyrazinyl, benzofuranyl, indolyl, isoquinolyl and quinolyl, or any said heterocyclic radical mono- or disubstituted on carbon by lower alkyl, lower alkoxy or halogen, or any said unsubstituted or substituted pyrrolyl or indolyl radical substituted on nitrogen by lower alkyl; R and $R_1$ independently represent hydrogen, lower alkyl, phenyl-lower alkyl or phenyl-lower alkyl substituted on phenyl by one or two radicals selected from lower alkyl, lower alkoxy, lower alkylmercapto, lower alkylsulfinyl, lower alkylsulfonyl, halogen and trifluoromethyl; $R_2$ and $R_3$ independently represent hydrogen, lower alkyl, halogen, trifluoromethyl or lower alkoxy; $R_4$ represents hydroxy; pharmaceutically acceptable salts thereof derived from pharmaceutically acceptable bases; or pharmaceutically acceptable acid addition salts thereof provided that Ar represents a basic heterocyclic radical; lower alkyl enol ether derivatives thereof; and lower alkanoyl enol ester derivatives thereof.

Further preferred is the embodiment represented by the compounds of formula I or tautomers thereof wherein n represents zero; Ar represents phenyl or phenyl monosubstituted by $C_1$-$C_4$-alkyl, $C_1$-$C_4$-alkoxy, $C_1$-$C_4$-alkylmercapto, $C_1$-$C_4$-alkylsulfinyl, $C_1$-$C_4$-alkylsulfonyl, halogen or trifluoromethyl, or phenyl disubstituted by radicals selected from $C_1$-$C_4$-alkyl, $C_1$-$C_4$-alkoxy and halogen; R represents hydrogen, $C_1$-$C_4$alkyl, phenyl-$C_1$-$C_4$-lower alkyl or phenyl-$C_1$-$C_4$-alkyl monosubstituted on phenyl by $C_1$-$C_4$-alkyl, $C_1$-$C_4$-alkoxy, $C_1$-$C_4$-alkylmercapto, $C_1$-$C_4$-alkylsulfinyl, $C_1$-$C_4$-alkylsulfonyl, halogen or trifluoromethyl, or phenyl-$C_1$-$C_4$-alkyl disubstituted on phenyl by radicals selected from $C_1$-$C_4$-alkyl, $C_1$-$C_4$-alkoxy and halogen; $R_1$ represents hydrogen, $C_1$-$C_4$-alkyl, phenyl-$C_1$-$C_4$-alkyl or phenyl-$C_1$-$C_4$-alkyl monosubstituted on phenyl by $C_1$-$C_4$-alkyl, $C_1$-$C_4$-alkoxy, $C_1$-$C_4$-alkylmercapto, $C_1$-$C_4$-alkylsulfinyl, $C_1$-$C_4$-alkylsulfonyl, halogen or trifluoromethyl, or phenyl-$C_1$-$C_4$-alkyl disubstituted on phenyl by radicals selected from $C_1$-$C_4$-alkyl, $C_1$-$C_4$-alkoxy and halogen; $R_2$ represents hydrogen, $C_1$-$C_4$-alkyl, $C_1$-$C_4$-alkoxy, halogen or trifluoromethyl; $R_3$ represents hydrogen, $C_1$-$C_4$-alkyl, $C_1$-$C_4$-alkoxy or halogen; $R_4$ represents hydroxy; and pharmaceutically acceptable salts derived from pharmaceutically acceptable bases.

Also preferred is the embodiment represented by the compounds of formula I or tautomers thereof wherein n represents zero; Ar represents a heterocyclic radical selected from 2-pyridyl and 2-thiazolyl, or said radical substituted on carbon by $C_1$-$C_4$-alkyl or halogen; R represents hydrogen, $C_1$-$C_4$-alkyl, phenyl-$C_1$-$C_4$-lower alkyl or phenyl-$C_1$-$C_4$-alkyl monosubstituted on phenyl by $C_1$-$C_4$-alkyl, $C_1$-$C_4$-alkoxy, $C_1$-$C_4$-alkylmercapto, halogen or trifluoromethyl, or phenyl-$C_1$-$C_4$-alkyl disubstituted on phenyl by radicals selected from $C_1$-$C_4$-alkyl, $C_1$-$C_4$-alkoxy and halogen; $R_1$ represents hydrogen, $C_1$-$C_4$-alkyl, phenyl-$C_1$-$C_4$-alkyl or phenyl-$C_1$-$C_4$-alkyl monosubstituted on phenyl by $C_1$-$C_4$-alkyl, $C_1$-$C_4$-alkoxy, $C_1$-$C_4$-alkylmercapto, halogen or trifluoromethyl, or phenyl-$C_1$-$C_4$-alkyl disubstituted on phenyl by radicals selected from $C_1$-$C_4$-alkyl, $C_1$-$C_4$-alkoxy and halogen; $R_2$ represents hydrogen, $C_1$-$C_4$-alkyl, $C_1$-$C_4$-alkoxy, halogen or trifluoromethyl; $R_3$ represents hydrogen, $C_1$-$C_4$-alkyl, $C_1$-$C_4$-alkoxy or halogen; $R_4$ represents hydroxy; and pharmaceutically acceptable salts thereof derived from pharmaceutically acceptable bases, or pharmaceutically acceptable acid-addition salts thereof.

Further preferred are the compounds of formula II

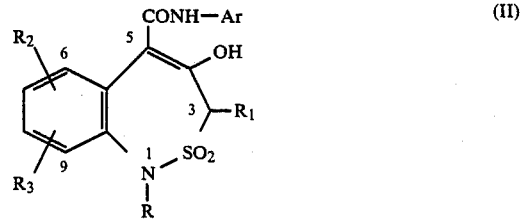

or tautomers thereof wherein Ar represents phenyl or phenyl monosubstituted by $C_1$-$C_4$-alkyl, $C_1$-$C_4$-alkoxy, $C_1$-$C_4$-alkylmercapto, halogen or trifluoromethyl; R represents $C_1$-$C_4$ alkyl, phenyl-$C_1$-$C_4$-alkyl or phenyl-$C_1$-$C_4$-alkyl monosubstituted on phenyl by halogen or trifluoromethyl; $R_1$ represents hydrogen, $C_1$-$C_4$-alkyl or phenyl-$C_1$-$C_4$-alkyl; $R_2$ represents hydrogen, halogen, trifluoromethyl or $C_1$-$C_4$-alkyl; $R_3$ represents hydrogen; and pharmaceutically acceptable salts derived from pharmaceutically acceptable bases.

Particularly preferred are the compounds of formula II or tautomers thereof, wherein Ar represents phenyl or phenyl monosubstituted by methyl, methylmercapto, methoxy, chloro, fluoro or trifluoromethyl; R represents methyl, benzyl or benzyl monosubstituted on phenyl by halogen or trifluoromethyl; $R_1$, $R_2$ and $R_3$ represent hydrogen; and pharmaceutically acceptable salts derived from pharmaceutically acceptable bases.

The general definitions used herein have the following meaning within the scope of the present invention.

The term "lower" referred to above and hereinafter in connection with organic radicals or compounds respectively defines such as branched or unbranched with up to and including 7, preferably up to and including 4 and advantageously one or two carbon atoms.

A lower alkyl group preferably contains 1-4 carbon atoms and represents for example ethyl, propyl, butyl or advantageously methyl.

A lower alkoxy group preferably contains 1-4 carbon atoms and represents for example ethoxy, propoxy, isopropoxy or advantageously methoxy; a lower alkylmercapto group preferably contains 1-4 carbon atoms and represents advantageously methylmercapto or ethylmercapto; a lower alkylsulfinyl group preferably contains 1-4 carbon atoms and represents advantageously methylsulfinyl or ethylsulfinyl; a lower alkylsulfonyl group preferably contains 1-4 carbon atoms and represents advantageously methylsulfonyl or ethylsulfonyl.

Halogen preferably represents chloro or fluoro but may also be bromo or iodo.

An aryl radical (Ar) represents a carbocyclic or a heterocyclic aryl radical.

A carbocyclic aryl radical represents preferably phenyl or phenyl mono- or di-substituted by one or two radicals selected from lower alkyl, lower alkoxy, lower alkylmercapto, lower alkylsulfinyl, lower alkylsulfonyl, halogen, cyano, carboxy, lower alkoxycarbonyl, carbamoyl and trifluoromethyl; or 1- or 2-naphthyl.

A heterocyclic aryl radical, particularly Ar in the $CONH(CH_2)_n$-Ar moiety, is preferably bonded on carbon to the $CONH(CH_2)_n$ radical, that is to a $CH_2$ carbon when n represents 1 or 2 or to the amide nitrogen when n represents zero.

A heterocyclic aryl radical represents preferably an aromatic radical such as furyl, pyrrolyl, thienyl, thiazolyl, oxazolyl, pyridyl, pyrimidyl, pyrazinyl, benzofuranyl, indolyl, isoquinolyl or quinolyl, but may also represent imidazolyl, isoxazolyl, benzimidazolyl, benzoxazolyl or any said heterocyclic radical mono- or disubstituted on carbon by lower alkyl, lower alkoxy or halogen, or any of said unsubstituted or substituted pyrrolyl, indolyl, imidazolyl or benzimidazolyl radical further substituted on nitrogen by lower alkyl.

Furyl represents preferably 2-furyl.
Pyrrolyl represents preferably 2-pyrrolyl.
Thienyl represents preferably 2-thienyl.
Thiazolyl represents preferably 2-thiazolyl.
Oxazolyl represents preferably 2-oxazolyl.
Pyridyl represents preferably 2- or 4-pyridyl, advantageously 2-pyridyl.
Pyrimidyl represents preferably 2-pyrimidyl.
Pyrazinyl represents preferably 2-pyrazinyl.
Benzofuranyl represents preferably 2-benzofuranyl.
Indolyl represents preferably 2-indolyl.
Isoquinolyl represents preferably 4-isoquinolyl.
Quinolyl represents preferably 4-quinolyl.

Lower alkanoyl represents preferably $C_1$-$C_4$-alkanoyl such as acetyl or propionyl.

The compounds of formula I wherein $R_4$ represents hydroxy have acidic properties and form lower alkyl enol ethers, lower alkanoyl enol esters, or salts thereof. Pharmaceutically acceptable salts are formed with pharmaceutically acceptable bases, such as alkali metal, alkaline earth metal, copper or zinc hydroxides, ammonia, mono-, di- or tri-lower (alkyl or hydroxyalkyl)-amines, monocyclic amines or alkylene-diamines, and are e.g. the sodium, potassium, magnesium, ammonium, mono-, di- or tri-(methyl, ethyl or hydroxyethyl)-ammonium, pyrrolidinium, ethylenediammonium or morpholinium salts.

Pharmaceutically acceptable salts of the compounds of the invention carrying a basic group are acid addition salts, which are preferably such of therapeutically acceptable inorganic or organic acids, such as strong mineral acids, for example hydrohalic, e.g. hydrochloric or hydrobromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric pyruvic, phenylacetic, benzoic, 4-aminobenzoic, anthranilic, 4-hydroxybenzoic, salicyclic, 4-aminosalicyclic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The compounds of the invention exhibit valuable pharmacological properties in mammals, primarily as inhibitors of the chemotactic activation of neutrophils; they are also active as selective 5-lipoxygenase inhibitors and as inhibitors of cartilage matrix degradation.

The compounds of the invention are therefore useful for the treatment and amelioration of diseases in mammals in which excessive neutrophil activation, excessive lipoxygenase activity or excessive cartilage degradation are implicated. Neutrophil activation is implicated e.g. in rheumatoid arthritis, 5-lipoxygenase e.g. in various allergic conditions and asthma, and cartilage degradation e.g. in osteoarthritis.

The above-cited properties are demonstrable in in vitro and in vivo tests, using advantageously mammals, e.g. mice, guinea pigs, dogs, rabbits or isolated organs, tissues, and enzyme preparations thereof, as well as cells and fluids isolated from human blood. Said compounds can be applied in vitro in the form of solutions, e.g. preferably aqueous solutions, and in vivo either enterally or parenterally, advantageously orally, e.g. as a suspension or in aqueous solution. The dosage in vitro may range between about $10^{-4}$ molar and $10^{-9}$ molar concentrations. The dosage in vivo may range depending on the route of administration, between about 0.01 and 50 mg/kg, advantageously between about 0.10 and 25 mg/kg.

The inhibition of the chemotactic activation of neutrophils is determined in vitro, e.g. by measuring the inhibition of the binding of f-MLP (formyl-methionyl-leucyl-phenylalanine) to human neutrophils in vitro as follows:

Human neutrophils are isolated by a modification of the procedure of Ferrante and Thong (J. Immunol. Methods 24:389, 1978). Red cells remaining in the neutrophil preparation are lysed by separate treatments with 0.83% $NH_4Cl$ and 0.1M tris-HCl, pH 7.5. Neutrophils are incubated in Hanks' buffer at 0° C. for 60 minutes with 15 nM $^3$H-f-MLP and test compound. Aliquots of the incubates are filtered and total $^3$H-f-MLP bound is measured. Non-specific binding in the presence of excess non-radioactive f-MLP is substracted, and percent inhibition of binding by the test drug is calculated. Final concentrations of solvents such as dimethylacetamide or ethanol which may be used to dissolve the test compound cannot exceed 1% in the incubation mixture.

The inhibition of the chemotactic activation of neutrophils can also be determined in vivo by measuring the inhibition of the accumulation of neutrophils into carrageenin impregnated polyurethane sponges after oral administration in the rat.

Lipoxygenase inhibition is determined e.g. by measuring the percent inhibition of the synthesis of 5-HETE [(5S)-5-hydroxy-6,8,11,14-eicosa-tetraenoic acid] and leukotriene $B_4$ ($LTB_4$, 5,12-dihydroxy-6,8,10,14-eicosatetraenoic acid) in A-23187-stimulated guinea pig polymorphonuclear leukocytes, essentially according to radiometric thin-layer chromatographic assays described by Walker and Dawson (J. Pharm. Pharmacol. 31: 778, 1979) and Jakschik and Lee (nature 287: 51, 1980) used to measure the formation of 5-HETE and $LTB_4$-like products from $^{14}$C-arachidonic acid.

Furthermore inhibition of the formation of leukotrienes and 5-HETE is determined e.g. by measuring their concentration in whole blood after oral administration in rats.

Antiinflammatory activity is determined by measuring the inhibition of the edema and of the mononuclear cell influx after oral administration in the rat model in which pleurisy is first induced by injecting carrageenin into the pleural cavity, e.g. according to A. P. Almeida et al., J. Pharmacol. Exp. Therap. 214, 74 (1980).

The inhibition of cartilage matrix degradation can be determined in vitro in the bovine nasal cartilage-synovium co-culture model of cartilage matrix degradation which is carried out as follows:

The proteoglycan matrix of bovine nasal septum cartilage is labeled in vitro by incorporation of $^{35}S$ into glycosaminoglycan. Cartilage slices are incubated overnight in a sulfate free medium containing $^{35}S$-sodium sulfate. $^{35}S$-Labeled cartilage slices are co-cultured with normal synovium explants in multiwell tissue culture plates. After 4 days incubation a 100μl aliquot of medium is counted. Cartilage slices are hydrolyzed and a 100μl aliquot of cartilage hydrolysate is counted. The percent $^{35}S$ released into the medium is determined and the percent inhibition of matrix degradation is calculated.

The inhibition of cartilage matrix degradation can also be similarly determined by measuring the decrease in proteoglycan release on synovial catabolin-induced degradation of bovine nasal cartilage.

Illustrative of the invention the compound of example 2 (as the sodium salt) is effective in inhibiting the binding of f-MLP to human neutrophils at a concentration of about $1 \times 10^{-6}M$. Furthermore, the compound effectively diminishes the accumulation of neutrophils into carrageenin-impregnated sponges in the rat at a dose of 25 mg/Kg p.o, effectively inhibits leukotriene and 5-HETE formation in whole rat blood at a dose of 50 mg/Kg p.o., significantly inhibits edema formation and mononuclear cell influx in the pleurisy model of inflammation at a dose of 10 mg/Kg p.o. in the rat, and inhibits at a concentration of about $1 \times 10^{-5}M$ the release of proteoglycan in catabolin-induced or synovium-induced degradation of cartilage.

In contrast to classical antiinflammatory agents, the compounds of the instant invention are not effective in the tests normally used for evaluating such agents, such as the carrageenin paw edema assay, the phenylquinone writhing assay and the established adjuvant arthritis test.

The aforementioned properties render the compounds of the invention useful particularly as disease-modifying antiinflammatory and antiarthritic agents, especially for the treatment and amelioration of inflammatory disorders, such as rheumatoid arthritis and osteoarthritis in mammals, including man.

The compounds of the invention can be prepared by synthetic processes comprising:

(a) condensing a ketone of the formula III

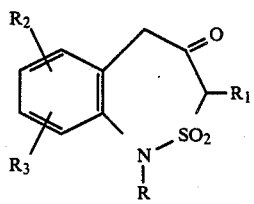
(III)

wherein R, $R_1$, $R_2$ and $R_3$ have meaning as defined above, or an enamine derivative of the formula IIIa

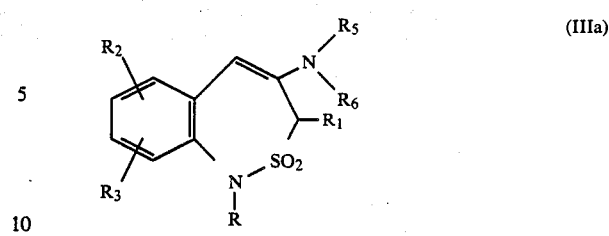
(IIIa)

wherein R, $R_1$, $R_2$, $R_3$, n have meaning as defined above, and $R_5$ and $R_6$ represent lower alkyl; or $R_5$ and $R_6$ together with the nitrogen to which they are attached represent pyrrolidino or piperidino, with a compound of the formula IV $$Ar\text{-}(CH_2)_n\text{-}N=C=O \qquad (IV)$$

wherein Ar and n have meaning as defined above;

(b) condensing a reactive functional derivative of a carboxylic acid of formula V

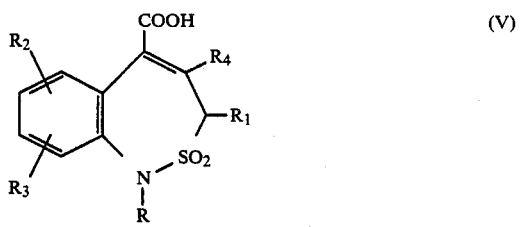
(V)

wherein R, $R_1$, $R_2$, $R_3$ and $R_4$ have meaning as defined above with an amine of the formula VI $$Ar\text{-}(CH_2)_n\text{-}NH_2 \qquad (VI)$$

wherein Ar and n have meaning as defined above;

(c) for compounds of formula I wherein $R_4$ represents hydroxy, cyclizing a reactive functional derivative of a carboxylic acid of the formula VII

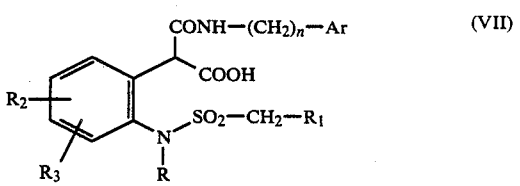
(VII)

wherein R, $R_1$, $R_2$, $R_3$, n and Ar have meaning as defined above;

(d) for compounds of formula I wherein $R_4$ represents hydroxy, cyclizing a reactive functional derivative of a carboxylic acid of the formula VIII

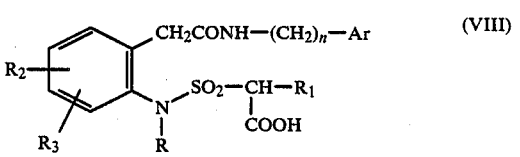
(VIII)

wherein R, $R_1$, $R_2$, $R_3$, n and Ar have meaning as defined above; optionally (e) for compounds of formula I wherein $R_4$ represents hydroxy, hydrolyzing an enamine of the formula IX

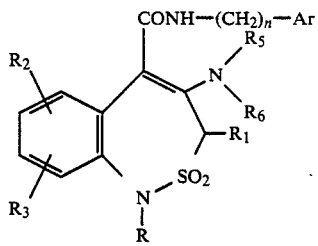

(IX)

wherein R, R₁, R₂, R₃, R₅, R₆ and n have meaning as defined above.

(f) and in addition, if required, converting a resulting compound of formula I obtained by any of the above processes into another compound of the invention; and optionally (g) converting any resulting compound into a salt or liberating the free compound from a salt thereof.

In the starting compounds and intermediates which are converted to the compounds of the invention in a manner described herein, functional groups present, such as amino and hydroxy, are optionally protected by conventional protecting groups that are common in preparative organic chemistry; protected amino and hydroxy groups are those that can be converted under mild conditions into free amino and hydroxy groups without the molecular framework being destroyed or other undesired side reactions taking place.

Well-known protecting groups that meet these conditions and their introduction and removal are described, for example, in J. F. W. McOmie, "Protective Groups in Organic Chemistry", Plenum Press, London, New York 1973, T. W. Green, "Protective Groups in Organic Synthesis", Wiley, New York 1984.

In the processes cited herein, reactive functional derivatives of carboxylic acids represent, for example, anhydrides especially mixed anhydrides, acid halides, acid azides, lower alkyl esters and activated esters thereof. Mixed anhydrides are preferably such from pivalic acid, or a lower alkyl (ethyl, isobutyl) hemiester of carbonic acid; acid halides are for example chlorides or bromides; activated esters are for example succinimido, phthalimido or 4-nitrophenyl esters; lower alkyl esters are for example the methyl or ethyl esters.

The condensation of a free carboxylic acid with an amine of formula VI in any of the processes cited herein, may be carried out in the presence of a condensing agent, e.g. diethyl phosphorocyanidate, 1,1'-carbonyldiimidazole or dicyclohexylcarbodiimide, in an inert polar solvent, such as dimethylformamide or methylene chloride.

Also, a reactive esterified derivative of an alcohol in any of the processes cited herein represents said alcohol esterified by a strong acid, especially a strong inorganic acid, such as a hydrohalic acid, especially hydrochloric, hydrobromic or hydriodic acid, or sulphuric acid, or by a strong organic acid, especially a strong organic sulfonic acid, such as an aliphatic or aromatic sulfonic acid, for example methanesulfonic acid, 4-methylphenylsulfonic acid or 4-bromophenylsulfonic acid. A said reactive esterified derivative is especially halo, for example chloro, bromo or iodo, or aliphatically or aromatically substituted sulfonyloxy, for example methylsulfonyloxy or 4-methylphenylsulfonyloxy (tosyloxy).

The condensation, according to process (a) of an isocyanate of formula IV with a ketone of formula III can be carried out in the presence of an inorganic or organic base, such as sodium hydride or triethylamine in a polar solvent, such as an ether, e.g. diethyl ether or tetrahydrofuran, and/or an amide or sulfoxide, e.g. dimethylformamide or dimethyl sulfoxide, preferably at a temperature range of 25° to 100° C.

The condensation according to process (a) of an isocyanate of formula IV with an enamine of formula IIIa can be carried out in an inert solvent such as toluene, preferably at or near room temperature.

In a preferred procedure according to process (a) for the preparation of compounds of formula I wherein R₄ represents hydroxy, a ketone of formula III is first converted to the corresponding enamine of formula IIIa using procedures well-known in the art, e.g. by treatment with a secondary amine, preferably with a cyclic lower alkyleneimine preferably pyrrolidine, in an inert water immiscible solvent such as toluene in an inert atmosphere, optionally using an acid catalyst such as p-toluenesulfonic acid, preferably at the boiling point of the solvent so as to separate from the reaction mixture the water that is liberated. The resulting enamine is then condensed, advantageously in situ, with an isocyanate of formula IV, advantageously at room temperature, to yield an enamine derivative of a compound of the invention, e.g. a compound of the formula IXa

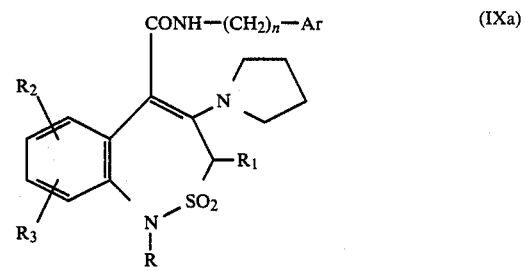

(IXa)

wherein R, R₁, R₂, R₃, n, Ar have meaning as defined above, which is in turn hydrolyzed according to process (e) to a compound of formula I wherein R₄ represents hydroxy on treatment with e.g. aqueous acid, such as hydrochloric acid.

The starting materials of formula III are advantageously prepared as follows:

A lower alkyl ester of an appropriate ortho-R₁—CH₂SO₂NH-substituted phenylacetic acid is reacted with a reactive esterified derivative of an alcohol corresponding to the radical R (if R does not represent hydrogen), e.g. with a halo derivative thereof, under standard alkylation reaction conditions, e.g. in dimethylformamide or tetrahydrofuran, in the presence of a base such as potassium carbonate, to yield a lower alkyl ester of a carboxylic acid of formula X

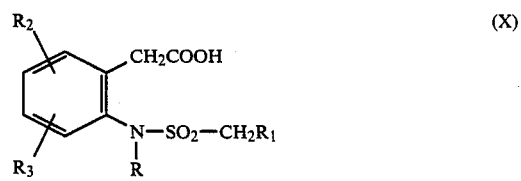

(X)

in which R and R₁-R₃ have meaning as previously defined.

Said lower alkyl ester (or other reactive functional derivative) of the carboxylic acid of formula X is then cyclized in the presence of a strong base, such as sodium hydride in an anhydrous inert polar solvent such as tetrahydrofuran, to obtain the correspondingly substituted bicyclic ketone of formula III.

The condensation according to process (b) can be carried out using advantageously a lower alkyl ester as the reactive functional derivative of the carboxylic acid of formula V. The amide formation is carried out by standard procedures known in the art, by condensing said ester with an amine of the formula VI at reflux temperature in a solvent such as toluene or xylene, advantageously with azeotropic removal of the lower alkanol liberated.

Starting with an ester of a compound of formula V and depending on the conditions and amount of amine of formula VI used, one obtains either a compound of formula I wherein $R_4$ represents hydroxy, or a compound of formula I wherein $R_4$ represents $NH(CH_2)_nAr$ in which n and Ar have meaning as defined above, or a mixture of said compounds.

A starting material, e.g. a lower alkyl ester, for example the ethyl ester of a carboxylic acid of formula V is advantageously prepared e.g. by first condensing, for example ethyl o-aminophenylacetate under standard conditions with e.g. a compound of the formula

(XI)

wherein $R_1$ has meaning as previously defined to yield a compound of the formula XII

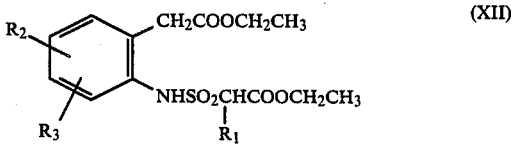

(XII)

wherein $R_1$, $R_2$ and $R_3$ have meaning as previously defined which then may first be treated with a reactive esterified derivative of an alcohol corresponding to the radical R (if R does not represent hydrogen) in the presence of e.g. potassium carbonate, and is subsequently cyclized with a strong base such as sodium ethoxide in an anhydrous medium to yield the ethyl ester of the corresponding compound of formula V wherein $R_4$ represents hydroxy.

The corresponding starting materials wherein $R_4$ represents $NR_5R_6$ may be obtained by condensation with the corresponding amine under conditions of enamine formation and separation of the derived compound from any resulting mixture.

The cyclization according to process (c) can be carried out by advantageously treating a lower alkyl ester of the carboxylic acid of formula VII with a strong base, e.g. sodium hydride in an anhydrous polar solvent such as dimethylformamide as described for intermediates under process (a).

The starting materials can be prepared as illustrated below.

Diethyl o-nitrophenylmalonate is first condensed with one mole equivalent of an amine of formula VI according to the general procedure of process (b), the resulting hemiester hemiamide is then hydrogenated to the corresponding aniline which may then first be treated with an aldehyde corresponding to the radical R (if R does not represent hydrogen) in the presence of e.g. sodium cyanoborohydride as the reducing agent, and is then reacted with a compound of the formula $R_1$—$CH_2SO_2Cl$ under standard conditions so as to yield the ethyl ester of a compound of formula VII.

The cyclization according to process (d) may be carried out by treating a reactive ester, e.g. the ethyl ester of a compound of the formula VIII, with a strong base, e.g. two equivalents of butyl lithium.

The starting materials, e.g. the ethyl ester of a compound of formula VIII, can be prepared as follows:

The appropriately N-substituted o-nitrophenylacetamide is first reduced to the corresponding aniline which may then first be converted to the R-substituted secondary amine by e.g. treatment with the aldehyde corresponding to the radical R (if R does not represent hydrogen) in the presence of e.g. sodium cyanoborohydride, and then condensing said amine with a compound of the formula XI.

The hydrolysis according to process (e) is preferably carried out by treatment with an aqueous acid such as hydrochloric acid. The starting materials of formula IX are prepared e.g. as described for compounds of formula IXa under process (a), or as described under process (b) and in the examples.

Further starting materials, e.g. of formula IV and VI, are either known or are prepared according to methods well-known in the art.

The compounds of the invention, so obtained, can be converted into each other according to methods generally known per se.

Thus, for example, resulting compounds of formula I wherein $R_4$ represents hydroxy, (as enols) can be etherified, e.g. with lower diazoalkanes, or esterified, e.g. with lower alkanoic acid anhydrides.

Compounds of formula I wherein R represents hydrogen, particularly compounds wherein $R_4$ represents hydroxy, can be converted to compounds of formula I wherein R is a substituent as previously defined, under conditions known in the art for substituting a sulfonamide, e.g. by treatment with a reactive esterified derivative of an alcohol corresponding to the radical R, e.g. a halide, under basic conditions, e.g. in the presence of a base, such as potassium or sodium carbonate, in a polar solvent such as dimethylformamide.

Compounds of formula I wherein $R_4$ represents $NR_5R_6$ can be converted to compounds of formula I wherein $R_4$ represents hydroxy as described under process (e).

The above reactions are otherwise carried out according to standard methods, in the presence or absence of diluents, preferably such as are inert to the reagents and are solvents thereof, of catalysts, condensing or neutralization agents and/or inert atmospheres, at low temperatures, room temperature or elevated temperatures, at atmospheric or superatmospheric pressure.

The invention also comprises any modification of the above processes wherein a compound resulting as an intermediate at any stage thereof is used as starting material and the remaining steps are carried out, or the process is discontinued at any stage thereof, or in which the starting material is formed under the reaction conditions or is used in the form of its salts or reactive derivatives. In said processes of the invention those starting materials are advantageously selected which yield the above-described preferred embodiments of the invention.

The invention also relates to novel intermediates and processes for their manufacture.

Acidic compounds of the invention may be converted into salts with pharmaceutically acceptable bases, e.g. an aqueous alkali metal hydroxide, advantageously in the presence of an ethereal or alcoholic solvent, such as a lower alkanol. From the solutions of the latter, the salts may be precipitated with ethers, e.g. diethyl ether. Basic compounds of the invention may be converted into acid addition salts, e.g. by treatment with the appropriate acid, e.g. in alcoholic solution. Resulting salts may be converted into the free compounds by treatment with acids or bases. These or other salts can also be used for purification of the compounds obtained. In view of the close relationship between the free compounds and the compounds in the form of their salts, whenever a compound is referred to in this context, a corresponding salt is also intended provided such is possible or appropriate.

The compounds, including their salts, can also be obtained in the form of their hydrates, or include other solvents used for the crystallization.

In case mixtures of any of the above compounds or intermediates are obtained, these can be separated into the single compounds by methods in themselves known, e.g. by fractional distillation, crystallization or chromatography.

Any racemic products of the invention or intermediates can be resolved into the optical antipodes, for example, by separation of diastereomeric salts formed from optically active acids or bases.

The present invention also relates to pharmaceutical compositions, especially pharmaceutical compositions suitable for the treatment and amelioration of inflammatory disorders, e.g. rheumatoid arthritis and osteoarthritis, in mammals.

Said pharmaceutical compositions according to the invention are those suitable for enteral, such as oral or rectal, transdermal and parenteral administration to mammals, including man, for the alleviation and treatment of inflammatory and arthritic disorders such as osteoarthritis and rheumatoid arthritis comprising an effective amount of a pharmacologically active compound of the invention in combination with one or more pharmaceutically acceptable carriers.

The pharmacologically active compounds of the invention are incorporated into pharmaceutical compositions comprising an effective amount thereof in conjunction or admixture with excipients or carriers suitable for either enteral or parenteral applications. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salts and/or polyethylene glycol; for tablets also (c) binders, e.g. magnesium aluminum silicate, starch paste, gelatin, tragacanth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The present invention further relates to a method of e.g. inhibiting the chemotactic activation of neutrophils, or of inhibiting cartilage matrix degradation in mammals, and of treating disorders responsive thereto, which comprises administering to a mammal in need thereof an effective amount of a compound of the invention or of a pharmaceutical composition comprising a said compound in combination with one or more pharmaceutically acceptable carriers.

The invention further more particularly relates to a method of treating and ameliorating inflammatory and arthritic disorders in mammals, such as rheumatoid arthritis, which comprises administering to a mammal in need thereof an effective amount of a compound of the invention, or of a pharmaceutical composition comprising a compound of the invention in combination with one or more pharmaceutically acceptable carriers.

The dosage of active compound administered is dependent on the species of warm-blooded animal (mammal), the body weight, age and individual condition, and on the form of administration.

A unit dosage for a mammal of about 50 to 70 kg may contain between about 5 and 100 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by analytical methods, particularly spectroscopic characteristics (e.g. MS, IR, NMR).

In naming compounds of the invention, i.e. of formula I, the N-(nitrogen) substituent refers to the group $(CH_2)_nAr$ attached to the nitrogen of the $CONH(CH_2)_nAr$ moiety in formula I.

EXAMPLE 1

A mixture of 1-(4-chlorophenylmethyl)-1,5-dihydro-2,1-benzothiazepin-4(3H)-one-2,2-dioxide (1.97 kg) and pyrrolidine (421 g) in toluene (9.9 l) is stirred and refluxed under an atmosphere of nitrogen for 3 hours and the water formed is collected in a Dean-Stark trap. The solution is cooled to 5° in an ice bath. 4-Chlorophenylisocyanate (995 g) is added all at once with stirring, which is continued at room temperature for 16 hours. The mixture is cooled to 5° in an ice bath, filtered and washed with toluene (1.0 l). The filter cake is air-dried overnight to give N-(4-chlorophenyl)-1-(4-chlorophenylmethyl)-1,3-dihydro-4-(1-pyrrolidinyl)-2,1-benzothiazepine-5-carboxamide-2,2-dioxide, mp 190°–194°, the compound of formula I wherein $R_1$, $R_2$ and $R_3$ represent hydrogen, R represents 4-chlorophenylmethyl, n represents zero, Ar represents 4-chlorophenyl and $R_4$ represents 1-pyrrolidinyl.

The starting material is prepared as follows:

To a solution of 2-nitrophenylacetic acid (2.00 kg) in methanol (4 l) at room temperature is added concentrated sulfuric acid (71.0 ml) all at once. The solution is stirred and refluxed for 6 hours, then allowed to stand at room temperature overnight. After cooling in an ice bath to 7°, the solution is adjusted to pH 8 by the addition of concentrated ammonium hydroxide (150 ml), keeping the temperature below 10°. The solution is concentrated in vacuo to a volume of 2 l and is then admixed with dichloromethane (2.5 l). The combined solution is washed with water (2×500 ml) and brine (500 ml), dried over anhydrous magnesium sulfate, and evaporated to yield crude product which is distilled to give methyl 2-nitrophenylacetate, b.p. 116°–131° (0.2 mm Hg).

To a solution of methyl 2-nitrophenylacetate, (6.04 kg) in toluene (100 l) is added anhydrous magnesium sulfate (2.00 kg) and then 5% palladium-on-charcoal (125 g). The mixture is then stirred and hydrogenated, keeping the temperature below 40° by regulation of the stirring rate and input of hydrogen gas. After the addition is complete, the mixture is filtered. The filtrate containing methyl 2-aminophenylacetate is cooled to −20° and triethylamine (3.75 kg) is added all at once with stirring. This is followed by the slow addition of a solution of methanesulfonyl chloride (3.91 kg) in toluene (4.5L), keeping the temperature between −2° and 5°. After stirring at −2° for 1 hour, the mixture is filtered and washed with toluene (10 l). The filter cake is then slurried with water (90 l) for 90 minutes, filtered, and washed with water (45 l) and methanol (8 l). The solid is dried at 50° in vacuo overnight to yield methyl 2-(methylsulfonylamino)phenylacetate, mp 73°–75°.

To a solution of methyl 2-(methylsulfonylamino)phenylacetate (2.00 kg) in dimethylformamide (10 l), under an atmosphere of nitrogen, is added 4-chlorobenzyl chloride (1.37 kg) all at once, followed by anhydrous potassium carbonate (1.18 kg). The mixture is heated at 75° and stirred for 4 hours, then cooled to room temperature overnight at which time it is poured into water (50 l). The resulting precipitate is dissolved in dichloromethane (4 l). The dichloromethane solution is washed with brine (500 ml), dried over anhydrous magnesium sulfate and filtered. The filtrate is evaporated in vacuo to give a solid which is air-dried overnight and vacuum-dried (0.3 mm Hg) at room temperature to yield methyl 2-[N-(4-chlorophenylmethyl)-methylsulfonylamino]-phenylacetate mp 73°–75°.

To a solution of methyl 2-[N-(4-chlorophenylmethyl)methylsulfonylamino]-phenylacetate (1.00 kg) in dry tetrahydrofuran (8 l) is added sodium hydride (60% in oil, 120 g) all at once under an atmosphere of nitrogen. The mixture is then stirred and brought to reflux over a period of approximately 50 minutes. After an additional 40 minutes of reflux, an evolution of hydrogen gas begins and lasts for approximately 5–10 minutes. At this point, complete solution occurs and reflux is continued for an additional 15 minutes. The solution is cooled to 5° in an ice bath and to this is added glacial acetic acid (172 ml) over a period of 15 minutes, keeping the temperature below 10°, to achieve pH6. The solvent is evaporated in vacuo at 40°–50° and the residue is partitioned between dichloromethane (4 l) and water (1 l). The layers are separated and the organic layer is washed with water (1 l) and brine (1 l). After drying over anhydrous magnesium sulfate, the solution is filtered and the filtrate is concentrated in vacuo to a volume of 1.2 l and cooled in an ice bath. The solid is filtered and the filter cake is washed with anhydrous ether (300 ml) to give, after air-drying overnight, 1-(4-chlorophenylmethyl)-1,5-dihydro-2,1-benzothiazepin-4(3H)-one-2,2-dioxide, mp 147°–148°.

EXAMPLE 2

(a) A solution of 1.50 kg of N-(4-chlorophenyl)1-(4-chlorophenylmethyl)-1,3-dihydro-4-(1-pyrrolidinyl)2,1-benzothiazepine-5-carboxamide-2,2-dioxide in dichloromethane (15.0 l) is admixed with 6 N hydrochloric acid (1.43 l) and the two-phase mixture is stirred and refluxed overnight. The layers are separated and the organic layer is washed with water (4.0 l) and brine (2.0 l), dried over anhydrous magnesium sulfate, and filtered. The filtrate is concentrated in vacuo to a volume of 3.5 l and to this is added an equal volume of ether. The mixture is stirred for 15 minutes, filtered and the filter cake is washed with anhydrous ether (500 ml). The product is dried overnight at 105°–110°/0.3 mm Hg to yield N-(4-chlorophenyl)-1-(4-chlorophenylmethyl)-1,3-dihydro-4-hydroxy-2,1-benzothiazepine5-carboxamide-2,2-dioxide, mp 182°–183°, as a hydrate containing ½ mole equivalent of water, being the compound of formula II wherein $R_1$, $R_2$ and $R_3$ represent hydrogen, R represents 4-chlorophenylmethyl and Ar represents 4-chlorophenyl.

(b) A slurry of 814.0 g of N-(4-chlorophenyl)-1-(4-chlorophenylmethyl)-1,3-dihydro-4-hydroxy-2,1-benzothiazepine-5-carboxamide-2,2-dioxide in absolute ethanol (3.0 l) is stirred under an atmosphere of nitrogen at room temperature, while a solution of sodium hydroxide (65.4 g) in water (163 ml) is added in a thin stream over a period of 20 minutes. The stirring is continued for 1.5 hours, and the small amount of insoluble material is removed by filtration through a pad of filter-cel. The filtrate is concentrated to dryness at 40°–50° under reduced pressure and the residue is further dried at room temperature (2–3 mm Hg) overnight. The crisp white foam that is obtained is ground in a mill using a 1.0 mm screen. The finely powdered product is dried at room temperature in a hood for 6 days to obtain N-(4-chlorophenyl)-1-(4-chlorophenylmethyl)-1,3-dihydro-4-hydroxy-2,1-benzothiazepine-5-carboxamide-2,2-dioxide sodium salt, mp 209°–210° dec. as a hydrate containing 1½ moles equivalent of water.

Similarly prepared are the zinc salt, mp>250°, the cupric salt, mp >250° and the magnesium salt, mp 394°–395° dec.

EXAMPLE 3

A stirred mixture of 3 g of ethyl 1-(4-chlorophenylmethyl)-1,3-dihydro-4-hydroxy-2,1-benzothiazepine-5-carboxylate-2,2-dioxide, 1.04 g of 4-chloroaniline and 100 ml of toluene is heated at reflux temperature for 18 hours. On cooling to room temperature, the solvent is removed by evaporation under reduced pressure and the residue is dissolved in 200 ml of ether, treated with charcoal, filtered and diluted with hexane whereupon N-(4-chlorophenyl)-1-(4-chlorophenylmethyl)-1,3-dihydro-4-hydroxy-2,1-benzothiazepine-5-carboxamide-2,2-dioxide crystallizes and is collected by filtration; m.p. 182°–183°.

The starting material is prepared as follows:

To a solution of 82.7 g of methyl 2-aminophenylacetate (see Example 1) in 1.2 l of toluene is added 42 ml of pyridine and the mixture is stirred at room temperature. To this mixture is added a solution of 93.2 g of ethoxycarbonylmethylsulfonyl chloride in 150 ml of toluene in a dropwise manner over a period of 30 minutes, maintaining the temperature of the reaction below 10° by means of an ice-water bath. After stirring at 0° for an additional 1 hour, the mixture is poured into 50 ml of ice-water, the organic layer is separated and washed with 150 ml of cold dilute hydrochloric acid followed by 150 ml of brine. The toluene extract is dried over anhydrous magnesium sulfate, filtered and the solvent evaporated under reduced pressure to yield methyl 2-(ethoxycarbonylmethylsulfonylamino)-phenylacetate as an oil which is used in the next step without further purification.

To a solution of 54.6 g of methyl 2-(ethoxycarbonylmethylsulfonylamino)-phenylacetate in 300 ml dimethylformamide under an atmosphere of nitrogen is added 28 g of 4-chlorobenzyl chloride followed by 35 g of anhydrous potassium carbonate. The mixture is heated at 75° and stirred for 1 hour, then allowed to cool to room temperature at which time it is poured into 1 liter of water. The mixture is then extracted with 2×300 ml of ether and the combined ethereal extracts are washed with 250 ml of brine, separated and dried over anhydrous magnesium sulfate. The solvent is then evaporated under reduced pressure and the residue of methyl 2-[N-(4-chlorophenylmethyl)-ethoxycarbonylmethylsulfonylamino]-phenylacetate is crystallized from a mixture of ether - hexane (4:1); m.p. 86°-88°.

This same intermediate may also be prepared by the following alternate route:

(a) A mixture of 31.5 g of methyl 2-aminophenylacetate and 26.8 g of 4-chlorobenzaldehyde is combined and heated under high vacuum at 50° to remove water and methyl 2-(4-chlorophenylmethyleneimino)-phenylacetate is obtained as an oil which is used in the next step without further purification.

(b) To a cooled and stirred mixture of 52.5 g of methyl 2-(4-chlorophenylmethyleneimino)-phenylacetate in 350 ml ethyl acetate is added 180 ml cold methanol followed by 9.2 g of sodium cyanoborohydride and 25 ml of ethanolic HCl. Stirring at 0° is continued for an additional 4 hours and the reaction is then allowed to warm to room temperature. The solvent is removed by evaporation under reduced pressure and the residue poured into 500 ml ice-water; the mixture is basified with dilute sodium hydroxide and extracted with 3×350 ml of ether. The combined ethereal extracts are separated, washed with 2×250 ml brine, dried over anhydrous magnesium sulfate, filtered and the solvent evaporated under reduced pressure to yield methyl 2-(4-chlorophenylmethylamino)-phenylacetate as an amber oil that is used in the next step without further purification.

(c) To a stirred solution of 48 g of methyl 2-(4-chlorophenylmethylamino)-phenylacetate in 1.2 l of toluene containing 26 ml of triethylamine is added 31 g of ethoxycarbonylmethylsulfonyl chloride in 50 ml of toluene in a dropwise manner over a period of 15 minutes maintaining the temperature of the reaction below 10°. The reaction mixture is then allowed to stir overnight at room temperature and poured into 2 l of ice-water and the organic layer separated. The toluene extracts are washed with 3×750 ml brine, separated, dried over anhydrous magnesium sulfate, filtered and the solvent evaporated under reduced pressure to yield 40 g of methyl 2-[N-(4-chlorophenylmethyl)-ethoxycarbonylmethylsulfonylamino]-phenylacetate which may be crystallized from ether-hexane (4:1); m.p. 86°-88°.

A solution of sodium ethoxide is prepared from the addition of 4 g of sodium spheres to 550 ml of anhydrous ethanol. To this solution is added 24 g of methyl 2-[N(4-chlorophenylmethyl)-ethoxycarbonylmethylsulfonylamino]phenylacetate and the reaction mixture is heated at reflux temperature for 18 hours. On cooling to room temperature, the ethanol is removed by evaporation under reduced pressure and the residue is poured into 750 ml ice-water, acidified with 5N HCl and the mixture extracted with 3×500 ml ether. The combined ethereal extracts are washed with 2×350 ml brine, separated, dried over anhydrous magnesium sulfate, filtered and the solvent removed by evaporation under reduced pressure to yield ethyl 1-(4-chlorophenylmethyl)-1,3-dihydro-4-hydroxy-2,1-benzothiazepine-5-carboxylate-2,2-dioxide which may be crystallized from ethanol; m.p. 147°-149°.

EXAMPLE 4

Compounds which can be prepared in a manner analogous to the procedures described in the previous examples using appropriate starting materials:

(a) N-(2-pyridyl)-1-(4-chlorophenylmethyl)-1,3-dihydro-4-hydroxy-2,1-benzothiazepine-5-carboxamide-2,2-dioxide, mp 235°;

(b) N-phenyl-1-(4-chlorophenylmethyl)-1,3-dihydro-4-hydroxy-2,1-benzothiazepine-5-carboxamide-2,2-dioxide, mp 181°-183°;

(c) N-(4-methylthiophenyl)-1-(4-chlorophenylmethyl)-1,3-dihydro-4-hydroxy-2,1-benzothiazepine-5-carboxamide-2,2-dioxide, mp 183°-185°;

(d) N-(3-trifluoromethylphenyl)-1-(4-chlorophenylmethyl)-1,3-dihydro-4-hydroxy-2,1-benzothiazepine-5-carboxamide-2,2-dioxide, mp 156°-158°;

(e) N-(2-thiazolyl)-1-(4-chlorophenylmethyl)-1,3-dihydro-4-hydroxy-2,1-benzothiazepine-5-carboxamide-2,2-dioxide, mp 175°-177°;

(f) N-(4-chlorophenyl)-1-(4-chlorophenylmethyl)-8-trifluoromethyl-1,3-dihydro-4-hydroxy-2,1-benzothiazepine-5-carboxamide-2,2-dioxide, mp 74°-75°;

(g) N-(4-chlorophenyl)-1-(4-chlorophenylmethyl)-7,8-dimethoxy-1,3-dihydro-4-hydroxy-2,1-benzothiazepine-5-carboxamide-2,2-dioxide, mp 248°-250°;

(h) N-(4-methylthiophenyl)-1-(4-chlorophenylmethyl)-8-trifluoromethyl-1,3-dihydro-4-hydroxy-2,1-benzothiazepine-5-carboxamide-2,2-dioxide, mp 193°-195°;

(i) N-(4-chlorophenyl)-1-(4-chlorophenylmethyl)-3-methyl-1,3-dihydro-4-hydroxy-2,1-benzothiazepinecarboxamide-2,2-dioxide, mp 190°-192°;

(j) N-(4-chlorophenyl)-1-(4-chlorophenylmethyl)-(phenylmethyl)-1,3-dihydro-4-hydroxy-2,1-benzothiazepine-5-carboxamide-2,2-dioxide, mp 186°-188°;

(k) N-(4-chlorophenyl)-1-(2-phenylethyl)-1,3-dihydro-4-hydroxy-2,1-benzothiazepine-5-carboxamide-2,2-dioxide, mp 179°-181°;

(l) N-(4-chlorophenyl)-1-(3,4-dichlorophenylmethyl)-1,3-dihydro-4-hydroxy-2,1-benzothiazepine-5-carboxamide 2,2-dioxide, mp 157°-159°;

(m) N-(4-chlorophenyl)-1-phenylmethyl-1,3-dihydro-4-hydroxy-2,1-benzothiazepine-5-carboxamide-2,2-dioxide, mp 182°-184°;

(n) N-(4-chlorophenyl)-1-(4-bromophenylmethyl)-1,3-dihydro-4-hydroxy-2,1-benzothiazepine-5-carboxamide-2,2-dioxide, mp 197°-199°;

(o) N-(2-carboxy-4-chlorophenyl)-1-(4-chlorophenyl-methyl)-1,3-dihydro-4-hydroxy-2,1-benzothiazepine-5-carboxamide-2,2-dioxide, mp 208°–210°;

(p) N-(2-thiazolyl)-1-methyl-1,3-dihydro-4-hydroxy-2,1-benzothiazepine-5-carboxamide-2,2-dioxide, mp 235°–237°;

(q) N-(3,4-dichlorophenylmethyl)-1-(4-chlorophenyl-methyl)-1,3-dihydro-4-hydroxy-2,1-benzothiazepine-5-carboxamide-2,2-dioxide, mp 164°–166°.

EXAMPLE 5

A mixture of 1.7 g of ethyl 1-(3,4-dichlorophenylmethyl)-1,3-dihydro-4-hydroxy-2,1-benzothiazepine-5-carboxylate-2,2-dioxide, 0.6 g of 4-chlorophenethylamine in 100 ml of toluene is heated at reflux for 2 days. The reaction mixture is evaporated to dryness. The residue is crystallized from ether - hexane (charcoal) to yield N-(4-chlorophenethyl)-1-(3,4-dichlorophenylmethyl)-1,3-dihydro-4-(4-chlorophenethylamino)-2,1-benzothiazepine-5-carboxamide-2,2-dioxide; m.p. 119°–121°.

EXAMPLE 6

Preparation of 1,000 capsules each containing 10 mg of the active ingreadient:

Formula

| | |
|---|---|
| N—(4-chlorophenyl)-1-(4-chlorophenylmethyl)-1,3-dihydro-4-hydroxy-2,1-benzothiazepine-5-carboxamide-2,2-dioxide | 10.0 g |
| Lactose | 207.0 g |
| Modified starch | 80.0 g |
| Magnesium stearate | 3.0 g |

Procedure:

All the powders are passed through a screen with openings of 0.6 mm. Then the drug substance is placed in a suitable mixer and mixed first with the magnesium stearate, then with the lactose and starch until homogenous. No. 2 hard gelatin capsules are filled with 300 mg of said mixture each, using a capsule filling machine.

What is claimed is:

1. A compound of the formula

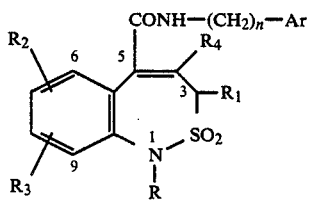

or a tautomer thereof wherein n prepresents zero; Ar represents phenyl or phenyl monosubstituted by $C_1$–$C_4$-alkyl, $C_1$–$C_4$-alkoxy, $C_1$–$C_4$-alkylmercapto, $C_1$–$C_4$-alkylsulfinyl, $C_1$–$C_4$-alkylsulfonyl, halogen or trifluoromethyl, or phenyl disubstituted by radicals selected from $C_1$–$C_4$-alkyl, $C_1$–$C_4$-alkoxy and halogen; R represents hydrogen, $C_1$–$C_4$-alkyl, phenyl-$C_1$–$C_4$-alkyl or phenyl-$C_1$–$C_4$-alkyl monosubstituted on phenyl by $C_1$–$C_4$-alkyl, $C_1$–$C_4$-alkoxy, $C_1$–$C_4$-alkylmercapto, $C_1$–$C_4$-alkylsulfinyl, $C_1$–$C_4$-alkylsulfonyl, halogen or trifluoromethyl, or phenyl-$C_1$–$C_4$-alkyl disubstituted on phenyl by radicals selected from $C_1$–$C_4$-alkyl, $C_1$–$C_4$-alkoxy and halogen; $R_1$ represents hydrogen, $C_1$–$C_4$-alkyl, phenyl-$C_1$–$C_4$-alkyl or phenyl-$C_1$–$C_4$-alkyl monosubstituted on phenyl by $C_1$–$C_4$-alkyl, $C_1$–$C_4$-alkoxy, $C_1$–$C_4$-alkylmercapto, $C_1$–$C_4$-alkylsulfinyl, $C_1$–$C_4$-alkylsulfonyl, halogen or trifluoromethyl, or phenyl-$C_1$–$C_4$-alkyl disubstituted on phenyl by radicals selected from $C_1$–$C_4$-alkyl, $C_1$–$C_4$-alkoxy and halogen; $R_2$ represents hydrogen, $C_1$–$C_4$-alkyl, $C_1$–$C_4$-alkoxy, halogen or trifluoromethyl; $R_3$ represents hydrogen, $C_1$–$C_4$-alkyl, $C_1$–$C_4$-alkoxy or halogen; $R_4$ represents hydroxy; or a pharmaceutically acceptable salt thereof, 2. A compound according to claim 1 of the formula

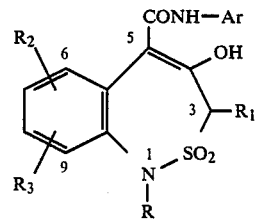

or a tautomer thereof wherein Ar represents phenyl or phenyl monosubstituted by $C_1$–$C_4$-alkyl, $C_1$–$C_4$-alkoxy, $C_1$–$C_4$-alkylmercapto, halogen or trifluoromethyl; R represents $C_1$–$C_4$-alkyl, phenyl-$C_1$–$C_4$-alkyl or phenyl-$C_1$–$C_4$-alkyl monosubstituteo on phenyl by halogen or trifluorome ; $R_1$ represents hydrogen, $C_1$–$C_4$-alkyl or phenyl-$C_1$–$C_4$-alkyl; $R_2$ represents hydrogen, halogen, trifluoromethyl or C $R_3$ represents hydrogen; or a pharmaceutically acceptable salt thereof.

3. A compound according to claim 2 of formula II, or tautomer thereof, wherein Ar represents phenyl or phenyl monosubstituted by methyl, methylmercapto, methoxy, chloro, fluoro or trifluoromethyl; R represents methyl, benzyl or benzyl monosubstituted on phenyl by halogen or trifluoromethyl; $R_1$, $R_2$ and $R_3$ represent hydrogen; or a pharmaceutically acceptable salt thereof.

4. A compound according to claim 2 being N-(4-chlorophenyl)-1-(4-chlorophenylmethyl)-1,3-dihydro-4-hydroxy-2,1-benzothiazepine-5-carboxamide-2,2-dioxide or a pharmaceutically acceptable salt thereof.

5. A compounds according to claim 1 being N-phenyl-1-(4-chlorophenylmethyl)-1,3-dihydro-4-hydroxy-2,1-benzothiazepine-5-carboxamide-2,2-dioxide or a pharmaceutically acceptable salt thereof.

6. A pharmaceutical composition suitable for inhibiting the chemotactic activation of neutrophils in mammals which comprises an effective neutrophil chemotactic activation inhibiting amount of a compound of claim 1 or of a said compound in combination with one or more pharmaceutically acceptable carriers.

7. A method of inhibiting the chemotactic activation of neutrophils in mammals which comprises administering to a mammal in need thereof an effective neutrophil chemotactic activation inhibiting amount of a compound of claim 1 or of a said compound in combination with one or more pharmaceutically acceptable carriers.

8. A method of inhibiting the chemotactic activation of neutrophils in mammals which comprises administering to a mammal in need thereof an effective neutrophil chemotactic activation inhibiting amount of a compound of claim 4 or of a said compound in combination with one or more pharmaceutically acceptable carriers.

9. A method of treating inflammatory disorders responsive to the inhibition of the chemotactic activation of neutrophils in mammals which comprises administering to a mammal in need thereof an effective neutrophil chemotactic activation inhibiting amount of a compound of claim 4 or of a said compound in combination with one or more pharmaceutically acceptable carriers.

10. A compound of the formula

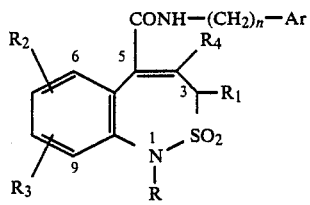

or a tautomer thereof wherein n represents zero; Ar represents a heterocyclic radical selected from 2-pyridyl and 2-thiazolyl, or said radical substituted on carbon by $C_1$-$C_4$-alkyl or halogen; R represents hydrogen, $C_1$-$C_4$-alkyl, phenyl-$C_1$-$C_4$-lower alkyl or phenyl-$C_1$-$C_4$alkyl monosubstituted on phenyl by $C_1$-$C_4$-alkyl, $C_1$-$C_4$-alkoxy, $C_1$-$C_4$-alkylmercapto, halogen or trifluoromethyl, or phenyl-$C_1$-$C_4$-alkyl disubstituted on phenyl by radicals selected from $C_1$-$C_4$-alkyl, $C_1$-$C_4$-alkoxy and halogen; $R_1$ represents hydrogen, $C_1$-$C_4$-alkyl, phenyl-$C_1$-$C_4$-alkyl or phenyl-$C_1$-$C_4$-alkyl monosubstituted on phenyl by $C_1$-$C_4$-alkyl, $C_1$-$C_4$-alkoxy, $C_1$-$C_4$-alkylmercapto, halogen or trifluoromethyl, or phenyl-$C_1$-$C_4$-alkyl disubstituted on phenyl by radicals selected from $C_1$-$C_4$-alkyl, $C_1$-$C_4$-alkoxy and halogen; $R_2$ represents hydrogen, $C_1$-$C_4$-alkyl, $C_1$-$C_4$-alkoxy, halogen or trifluoromethyl; $R_3$ represents hydrogen, $C_1$-$C_4$-alkyl, $C_1$-$C_4$-alkoxy or halogen; $R_4$ represents hydroxy; or a pharmaceutically acceptable salt thereof.

11. A compound according to claim 10 being N-(2-pyridyl)-1-(4-chlorophenylmethyl)-1,3-dihydro-4-hydroxy-2,1-benzothiazepine-5-carboxamide-2,2-dioxide or a pharmaceutically acceptable salt thereof.

12. A pharmaceutical composition suitable for inhibiting the chemotactic activation of neutrophils in mammals which comprises an effective neutrophil chemotactic activation inhibiting amount of a compound of claim 10 or of a said compound in combination with one or more pharmaceutically acceptable carriers.

13. A method of inhibiting the chemotactic activation of neutrophils in mammals which comprises administering to a mammal in need thereof an effective neutrophil chemotactic activation inhibiting amount of a compound of claim 10 or of a said compound in combination with one or more pharmaceutically acceptable carriers.

* * * * *

UNITED STATES PATENT AND TRADEMARK OFFICE
CERTIFICATE OF CORRECTION

PATENT NO. : 4,803,197
DATED : Feb. 7, 1989
INVENTOR(S) : Jan W.F. Wasley

It is certified that error appears in the above-identified patent and that said Letters Patent is hereby corrected as shown below:

Col. 19, Claim 1: Correct line 53 to read:

--or a tautomer thereof wherein n represents zero; Ar--

Col. 20, Claim 2: Correct lines 24-27 to read:

--$C_1$-$C_4$-alkyl monosubstituted on phenyl by halogen or trifluoromethyl; $R_1$ represents hydrogen, $C_1$-$C_4$-alkyl or phenyl-$C_1$-$C_4$-alkyl; $R_2$ represents hydrogen, halogen, trifluoromethyl or $C_1$-$C_4$-alkyl; $R_3$ represents hydrogen; or a phar- --

Col. 20, Claim 5: Correct line 40 to read:

--A compound according to claim 1 being N-phe --

Col. 22, Claim 10: Correct line 2 to read:

--phenyl-$C_1$-$C_4$-alkyl disubstituted on phenyl by radicals--

Signed and Sealed this

Seventeenth Day of April, 1990

Attest:

HARRY F. MANBECK, JR.

Attesting Officer     Commissioner of Patents and Trademarks